(12) United States Patent
Jevtic et al.

(10) Patent No.: US 9,051,235 B2
(45) Date of Patent: Jun. 9, 2015

(54) PROCESS FOR PRODUCING ETHANOL USING A MOLAR EXCESS OF HYDROGEN

(75) Inventors: Radmila Jevtic, Pasadena, TX (US); Victor J. Johnston, Houston, TX (US); David Lee, Seabrook, TX (US); Heiko Weiner, Pasadena, TX (US); Zhenhua Zhou, Houston, TX (US)

(73) Assignee: Celanese International Corporation, Irving, TX (US)

( * ) Notice: Subject to any disclaimer, the term of this patent is extended or adjusted under 35 U.S.C. 154(b) by 306 days.

(21) Appl. No.: 13/368,130

(22) Filed: Feb. 7, 2012

(65) Prior Publication Data

US 2013/0204049 A1 Aug. 8, 2013

(51) Int. Cl.
*C07C 27/04* (2006.01)
*C07C 29/149* (2006.01)
*C07C 51/12* (2006.01)
*C07C 51/44* (2006.01)

(52) U.S. Cl.
CPC .............. *C07C 29/149* (2013.01); *C07C 51/12* (2013.01); *C07C 51/44* (2013.01)

(58) Field of Classification Search
CPC ....................................................... C07C 27/04
USPC ........................................................ 568/885
See application file for complete search history.

(56) References Cited

U.S. PATENT DOCUMENTS

| | | |
|---|---|---|
| 2,607,807 A | 8/1952 | Ford |
| 2,649,407 A | 8/1953 | Harrison et al. |
| 2,882,244 A | 4/1959 | Milton |
| 3,102,150 A | 8/1963 | Hunter et al. |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,990,952 A | 11/1976 | Katzen et al. |
| 4,126,539 A | 11/1978 | Derr, Jr. et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,352,947 A | 10/1982 | Habib et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,443,639 A | 4/1984 | Pesa et al. |
| 4,454,358 A | 6/1984 | Kummer et al. |
| 4,456,775 A | 6/1984 | Travers et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,517,391 A | 5/1985 | Schuster et al. |
| 4,520,213 A | 5/1985 | Victor |
| 4,541,897 A | 9/1985 | Sommer et al. |
| 4,626,321 A | 12/1986 | Grethlein et al. |
| 4,626,604 A | 12/1986 | Hiles et al. |
| 4,628,130 A | 12/1986 | Bournonville et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,826,795 A | 5/1989 | Kitson et al. |
| 4,837,367 A | 6/1989 | Gustafson et al. |
| 4,837,368 A | 6/1989 | Gustafson et al. |
| 4,842,693 A | 6/1989 | Wheldon |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,008,235 A | 4/1991 | Wegman et al. |
| 5,026,908 A | 6/1991 | Smith et al. |
| 5,035,776 A | 7/1991 | Knapp |
| 5,047,592 A | 9/1991 | Carpenter |
| 5,061,671 A | 10/1991 | Kitson et al. |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,185,476 A | 2/1993 | Gustafson |
| 5,185,481 A | 2/1993 | Muto et al. |

(Continued)

FOREIGN PATENT DOCUMENTS

| | | |
|---|---|---|
| CA | 1233484 | 3/1988 |
| CN | 1230458 | 10/1999 |

(Continued)

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ZeaChem, Inc., Technology Overview, Lakewood, Colorado www.zeachem.com, 2008.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

(Continued)

*Primary Examiner* — Yong Chu
*Assistant Examiner* — Sonya Wright

(57) ABSTRACT

The present invention relates to a process for the production of ethanol using a molar excess of hydrogen. A mixed feed of acetic acid and ethyl acetate is fed to a reactor to be converted to ethanol. Hydrogen flow is increased to avoid a negative conversion of ethyl acetate.

16 Claims, 2 Drawing Sheets

(56) References Cited

U.S. PATENT DOCUMENTS

| | | |
|---|---|---|
| 5,198,592 A | 3/1993 | Van Beijnum et al. |
| 5,233,099 A | 8/1993 | Tabata et al. |
| 5,237,108 A | 8/1993 | Marraccini et al. |
| 5,243,095 A | 9/1993 | Roberts et al. |
| 5,250,271 A | 10/1993 | Horizoe et al. |
| 5,254,758 A | 10/1993 | Hiles et al. |
| 5,348,625 A | 9/1994 | Berg |
| 5,403,962 A | 4/1995 | Schneider et al. |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli et al. |
| 5,488,185 A | 1/1996 | Ramachandran et al. |
| RE35,377 E | 11/1996 | Steinberg et al. |
| 5,599,976 A | 2/1997 | Scates et al. |
| 5,821,111 A | 10/1998 | Grady et al. |
| 5,955,397 A | 9/1999 | Didillon et al. |
| 5,977,010 A | 11/1999 | Roberts et al. |
| 6,046,127 A | 4/2000 | Mimoun |
| 6,049,008 A | 4/2000 | Roberts et al. |
| 6,121,498 A | 9/2000 | Tustin et al. |
| 6,143,930 A | 11/2000 | Singh et al. |
| 6,232,352 B1 | 5/2001 | Vidalin |
| 6,294,703 B1 | 9/2001 | Hara et al. |
| 6,375,807 B1 | 4/2002 | Nieuwoudt et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,525,230 B2 | 2/2003 | Grosso |
| 6,627,770 B1 | 9/2003 | Cheung et al. |
| 6,657,078 B2 | 12/2003 | Scates et al. |
| 6,670,490 B1 | 12/2003 | Campos et al. |
| 6,685,754 B2 | 2/2004 | Kindig et al. |
| 6,693,213 B1 | 2/2004 | Kolena et al. |
| 6,723,886 B2 | 4/2004 | Allison et al. |
| 6,727,380 B2 | 4/2004 | Ellis et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,230,150 B2 | 6/2007 | Grosso et al. |
| 7,297,236 B1 | 11/2007 | Vander et al. |
| 7,351,559 B2 | 4/2008 | Verser et al. |
| 7,361,794 B2 | 4/2008 | Grosso |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,682,812 B2 | 3/2010 | Verser et al. |
| 7,700,814 B2 | 4/2010 | Garton et al. |
| 7,744,727 B2 | 6/2010 | Blum et al. |
| 7,863,489 B2 | 1/2011 | Johnston et al. |
| 2003/0004057 A1 | 1/2003 | Yamaguchi et al. |
| 2003/0077771 A1 | 4/2003 | Verser et al. |
| 2004/0232049 A1 | 11/2004 | Dath et al. |
| 2006/0019360 A1 | 1/2006 | Verser et al. |
| 2006/0127999 A1 | 6/2006 | Verser et al. |
| 2007/0031954 A1 | 2/2007 | Mairal et al. |
| 2007/0144886 A1 | 6/2007 | Sylvester et al. |
| 2007/0265360 A1 | 11/2007 | Luo et al. |
| 2007/0270511 A1 | 11/2007 | Melnichuk et al. |
| 2008/0135396 A1 | 6/2008 | Blum |
| 2008/0207953 A1 | 8/2008 | Houssin et al. |
| 2009/0014313 A1 | 1/2009 | Lee et al. |
| 2009/0023192 A1 | 1/2009 | Verser et al. |
| 2009/0081749 A1 | 3/2009 | Verser et al. |
| 2009/0166172 A1 | 7/2009 | Casey |
| 2009/0264285 A1 | 10/2009 | Luo et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0121114 A1 | 5/2010 | Weiner et al. |
| 2010/0168493 A1 | 7/2010 | Le Peltier et al. |
| 2010/0197485 A1 | 8/2010 | Johnston et al. |
| 2010/0197985 A1 | 8/2010 | Johnston et al. |
| 2010/0273229 A1 | 10/2010 | Verser et al. |
| 2011/0004033 A1 | 1/2011 | Johnston et al. |
| 2011/0082322 A1 | 4/2011 | Jevtic et al. |
| 2011/0098501 A1 | 4/2011 | Johnston et al. |
| 2011/0224462 A1 | 9/2011 | Ditzel et al. |
| 2012/0178975 A1 | 7/2012 | Weiner et al. |

FOREIGN PATENT DOCUMENTS

| | | |
|---|---|---|
| CN | 102228831 | 11/2011 |
| CN | 102229520 | 11/2011 |
| EP | 0087870 | 9/1983 |
| EP | 0104197 | 4/1984 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0285420 | 10/1988 |
| EP | 0456647 | 11/1991 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 6-116182 | 4/1994 |
| JP | 2001-046874 | 2/2001 |
| WO | WO 82/03854 | 11/1982 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063174 | 5/2009 |
| WO | WO 2009/063176 | 5/2009 |
| WO | WO-2009063176 * | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2010/014151 | 2/2010 |
| WO | WO 2010/014153 | 2/2010 |
| WO | WO 2010/055285 | 5/2010 |
| WO | WO 2011/053365 | 5/2011 |

OTHER PUBLICATIONS

International Search Report and Written Opinion mailed Apr. 5, 2013 in corresponding International Application No. PCT/US2012/067766.

Yang et al, Process of Ethanol Synthesis through esterification of acetic acid and economic analysis. No. 4, 2011.

T. Yokoyama, et al., "Carboxylic Acids and Derivatives", Fine Chemicals through Heterogenous Catalysis, pp. 370-379, (2008).

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Alcala, et al., (2005). Experimental and DFT studies of the conversion of ethanol and acetic acid on PtSn-based catalysts, Journal of Physical Chemistry, 109(6), 2074-2085.

(56) References Cited

OTHER PUBLICATIONS

Burkhanov, et al., "Palladium-Based Alloy Membranes for Separation of High Purity Hydrogen from Hydrogen-Containing Gas Mixtures", Platinum Metals Rev., 2011, 55, (1), pp. 3-12.

* cited by examiner

PROCESS FOR PRODUCING ETHANOL USING A MOLAR EXCESS OF HYDROGEN

FIELD OF THE INVENTION

The present invention relates generally to processes for producing ethanol via the hydrogenation of acetic acid, ethyl acetate, and mixtures thereof. In particular, the present invention relates to the use of a molar excess of hydrogen in the hydrogenation reaction.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The hydrogenation of alkanoic acid, e.g., acetic acid, and optionally the respective esters, yields a crude ethanol product that comprises impurities, e.g., water, which are often formed with ethanol or in side reactions. These impurities may limit the production of ethanol and may require expensive and complex purification trains to separate the impurities from the ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol product and a stream of acetic acid and ethyl acetate, which is recycled to the hydrogenation reactor.

Even in view of the conventional methods, the need remains for improved processes for efficiently producing ethanol from acetic acid and/or ethyl acetate.

SUMMARY OF THE INVENTION

The present invention relates to a process for the production of ethanol. The process comprises the step of reacting acetic acid, ethyl acetate, and hydrogen and in the presence of a catalyst and under conditions effective to form a crude ethanol product. The crude ethanol product may comprise ethanol, acetic acid, ethyl acetate, and water. Preferably, the reaction is conducted in a reactor and a molar ratio of hydrogen to acetic acid fed the reactor is greater than 12:1. In one embodiment, the process may further comprise the step of maintaining the reactants in the reactor for a residence time less than 20 seconds. The ethyl acetate conversion may be greater than or equal to 0%, e.g., the conversion is not negative and there is not a net increase in ethyl acetate under steady state conditions. The process further comprises the step of recovering ethanol from the crude ethanol product.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
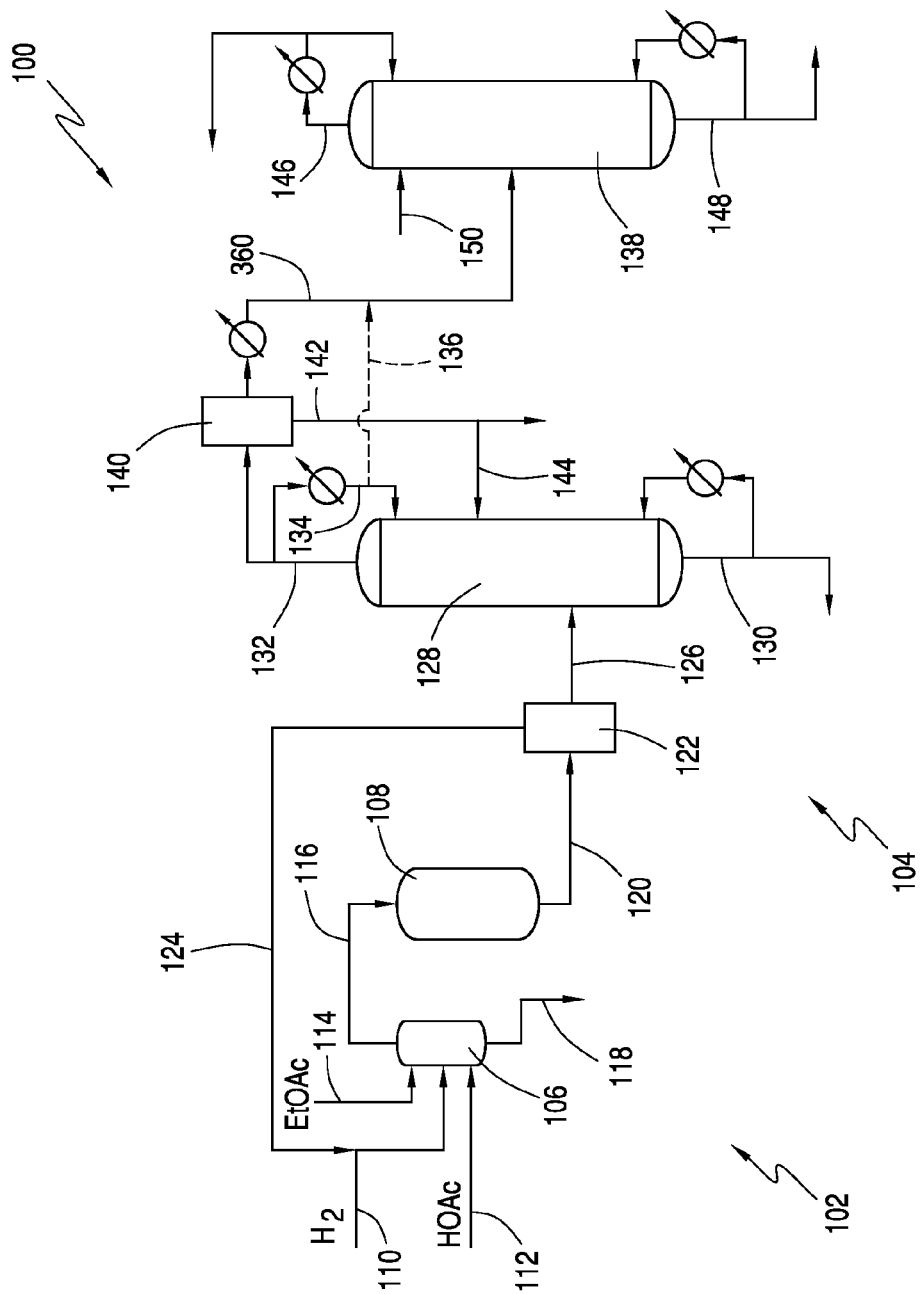
FIG. 1 is a schematic diagram of a hydrogenation/separation process in accordance with an embodiment of the present invention.

Acetic acid and ethyl acetate may be reacted with hydrogen, e.g., hydrogenated, to form a crude ethanol product. The crude ethanol product comprises ethanol, unreacted acetic acid and ethyl acetate, as well as various impurities, e.g., water. These impurities 1) limit the production of ethanol and 2) require expensive and complex purification trains to separate the impurities from the ethanol. To increase reaction efficiencies and avoid the production of impurities, conversion of the reactants, e.g., acetic acid and ethyl acetate, into ethanol is desired.

In some cases, when the hydrogenation process is operating at steady state, ethyl acetate is also fed to the reaction zone along with the fresh acetic acid. The ethyl acetate may be produced under hydrogenation conditions for reducing acetic acid to ethyl acetate and then recycled from the separation zone to the reaction zone as a vapor phase reactant. When the ethyl acetate in the vapor phase reactants is not consumed in the reactor and ethyl acetate is continuously formed, the conversion of ethyl acetate would be negative, which is not desired. This may lead to a buildup of ethyl acetate that would reduce the efficiency of producing ethanol.

Advantageously, the present invention may prevent negative conversion of ethyl acetate by increasing the hydrogen flow to the reactor relative to the acetic acid flow and the ethyl acetate flow. The increased hydrogen flow reduces the residence time of the reactants in the reactor. Normally, a reduction in residence time may be expected to decrease the conversion of acetic acid and/or ethyl acetate. However, surprisingly and unexpectedly, when hydrogen flow to the reactor is increased, a mixed feed of acetic acid and ethyl acetate is able to maintain a positive (or a non-negative) conversion of ethyl acetate, e.g., at least greater than 0% or greater than or equal to 0%, thus avoiding negative conversion of ethyl acetate. In addition, the conversion of acetic acid is not impacted by the increased flow of hydrogen and may be greater than 60%, e.g., greater than 70% or greater than 80%.

Accordingly, the present invention, in one embodiment, relates to a process for producing ethanol. The process comprises the step of reacting acetic acid, ethyl acetate, and hydrogen to form a crude ethanol product. The crude ethanol product comprises ethanol, water, acetic acid and, ethyl acetate. The reaction may be conducted in a reactor and in the presence of a catalyst. In preferred embodiments, due to the increase flow of hydrogen, the gas hourly space velocity (GHSV) may be from 180 $hr^{-1}$ to 50,000, e.g., from 240 $hr^{-1}$ to 35,000 $hr^{-1}$, or from 240 $hr^{-1}$ to 3,000 $hr^{-1}$. For example, the residence time of the reactants in the reactor is less than 20 seconds, e.g., less than 17 seconds or less than 15 seconds. The residence time may be from 0.1 to 20 seconds, e.g., from 0.5 to 17 seconds or from 1 to 15 seconds. In one embodiment, when four parallel reactors are employed, the residence time indicates the total residence time for all four reactors, in total.

In addition, the increased hydrogen flow may also increase the molar ratio of hydrogen to acetic acid in the reaction mixture that is fed to the reactor. In one embodiment, the molar ratio of hydrogen to acetic acid may be greater than 12:1, e.g., greater than 15:1 or greater than 20:1. Theoretically, the hydrogenation reaction consumes two moles of hydrogen per mole of acetic acid and the feed to the reactor would contain about 6.3 wt. % hydrogen. Due to the excess hydrogen with the increased flow rates, the mole percentage of hydrogen is preferably at least 20 wt. % hydrogen, e.g. at least 25 wt. % hydrogen or at least 30 wt. % hydrogen.

Hydrogenation of Acetic Acid

The process of the present invention may be used with any hydrogenation process for producing ethanol. Preferably, the catalyst may be capable of converting acetic acid and ethyl acetate to ethanol under hydrogenation conditions. The materials, catalysts, reaction conditions, and separation processes that may be used in the hydrogenation of acetic acid and/or ethyl acetate are described further below.

The raw materials, acetic acid, ethyl acetate, and/or hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,132,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process and/or the methanol carbonylation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

FIG. 1 is a diagram of a process 100 in accordance with the present invention. Process 100 comprises reaction zone 102 and separation zone 104. Reaction zone 102 comprises vaporizer 106 and reactor 108. In reaction zone 102, hydrogen and acetic acid are fed to vaporizer 106 via hydrogen feed line 110 and acetic acid feed line 112, respectively. In some embodiments, ethyl acetate may be fed to vaporizer 106 via ethyl acetate feed line 114. Although FIG. 1 shows ethyl acetate being fed via ethyl acetate feed line 114, in one embodiment, ethyl acetate may be fed to reactor 108 from a recycle stream from separation zone 104. In one embodiment, ethyl acetate may be present in the acetic acid feed. In one embodiment, two or more of the reactant feed lines may be combined and fed to vaporizer 106 (not shown). In one embodiment, lines 112 and 114 may be combined and fed to the vaporizer 106 (not shown). In one embodiment, additional hydrogen may be fed to reactor 108 via a separate hydrogen feed line(s), e.g., hydrogen feed line(s) different from hydrogen feed line 110 (not shown). In such cases, the additional hydrogen feed line(s) may provide increased hydrogen flow to the reactor.

The acetic acid and ethyl acetate feeds in lines 112 and 114 may be preheated to a temperature from 30° C. to 150° C., e.g., from 50° C. to 125° C. or from 60° C. to 115° C. The hydrogen feed may be fed at a pressure from 1200 kPa to 2100 kPa, e.g., from 1500 kPa to 2800 kPa, or 1700 kPa to 2600 kPa.

In one embodiment, the flow of liquid acetic acid fed to the vaporizer is maintained at a relatively constant level as the process is operated. The molar ratio of hydrogen to acetic acid may be achieved by adjusting the flow rate of hydrogen fed to vaporizer 106.

Vaporizer 106 may operate at a temperature of from 20° C. to 250° C. and at a pressure from 10 kPa to 2000 kPa. Vaporizer 106 produces vapor feed stream in line 116 by transferring the acetic acid, ethyl acetate, and water from the liquid to gas phase below the boiling point of acetic acid in reactor 108 at the operating pressure of the reactor. In one embodiment, the acetic acid in the liquid state is maintained at a temperature below 160° C., e.g., below 150° C. or below 130° C. Vaporizer 106 may be operated at a temperature of at least 118° C. Vaporizer 106 yields vapor feed stream 116 comprising hydrogen, acetic acid, and ethyl acetate, which is withdrawn from vaporizer 106 and fed to hydrogenation reactor 108.

The temperature of vapor feed stream 116 is preferably from 100° C. to 350° C., e.g., from 120° C. to 210° C. or from 150° C. to 200° C. In some embodiments, vapor feed stream 116 may comprise from 0.15 wt. % to 25 wt. % water. In addition, although FIG. 1 shows line 116 being directed to the top of reactor 108, line 116 may be directed to the side, upper portion, or bottom of reactor 108.

The temperature of feed stream in line 116 is preferably from 100° C. to 350° C., e.g., from 120° C. to 210° C. or from 150° C. to 200° C. A preheater may be used to further heat feed stream 116 to the reactor temperature.

Any feed that is not vaporized is removed from vaporizer 106 in a blowdown stream and may be recycled or discarded thereto. The mass ratio of feed stream in line 116 to blowdown stream may be from 6:1 to 500:1, e.g., from 10:1 to 500:1, from 20:1 to 500:1 or from 50:1 to 500:1.

In reactor 108, acetic acid and/or ethyl acetate are hydrogenated to form a crude ethanol product comprising ethanol and other compounds such as water, ethyl acetate, and acetic acid. The crude ethanol product exits reaction zone 102 via line 120. Separation zone 104 comprises flasher 122 and one or more separation units, e.g. distillation columns, for recovering ethanol from the crude ethanol product. Exemplary separation zones are discussed below.

In one embodiment, one or more guard beds (not shown) may be used upstream of the reactor, optionally upstream of the vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

The hydrogenation reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 200° C., or from 250° C. to 200° C. The pressure may range from 10 kPa to 2000 kPa, e.g., from 50 kPa to 1200 kPa, or from 100 kPa to 1500 kPa. The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Catalysts

The hydrogenation of acetic acid to form ethanol is preferably conducted in the presence of a hydrogenation catalyst in the reactor.

The catalysts of the invention preferably include at least one precious metal impregnated on the catalyst support. The precious metal may be selected, for example, from rhodium, rhenium, ruthenium, platinum, palladium, osmium, iridium and gold. Preferred precious metals for the catalysts of the invention include palladium, platinum, and rhodium. The precious metal preferably is catalytically active in the hydrogenation of a carboxylic acid and/or its ester to the corresponding alcohol(s). The precious metal may be in elemental form or in molecular form, e.g., an oxide of the precious metal. It is preferred that the catalyst comprises such precious metals in an amount less than 5 wt. %, e.g., less than 3 wt. %, less than 1 wt. % or less than 0.5 wt. %. In terms of ranges, the catalyst may comprise the precious metal in an amount from 0.05 to 10 wt. %, e.g. from 0.1 to 5 wt. %, or from 0.1 to 3 wt. %, based on the total weight of the catalyst.

In addition to the precious metal, the catalyst includes one or more active metals impregnated on the support. As used herein, the term "active metal" refers to a catalytically active metal, and may include precious or non-precious active metals. Thus, a catalyst comprising a precious metal and an active metal may include: (i) one (or more) precious metals and one (or more) non-precious active metals, or (ii) may comprise two (or more) precious metals. Thus, precious metals are included herein as exemplary active metals. Further, it should be understood that use of the term "active metal" to refer to some metals in the catalysts of the invention is not meant to suggest that the precious metal that is also included in the inventive catalysts is not catalytically active.

In one embodiment, the one or more active metals included in the catalyst are selected from the group consisting of copper, iron, cobalt, vanadium, nickel, titanium, zinc, chromium, molybdenum, tungsten, tin, lanthanum, cerium, and manganese, or from any of the aforementioned precious metals. Preferably, however, the one or more active metals do not include any precious metals. More preferably, the one or more active metals are selected from the group consisting of copper, iron, cobalt, nickel, chromium, molybdenum, tungsten and tin, and more preferably the one or more active metals are selected from cobalt, tin and tungsten. The one or more active metals may be in elemental form or in molecular form, e.g., an oxide of the active metal, or a combination thereof. The total weight of all the active metals, including the aforementioned precious metal, present in the catalyst preferably is from 0.1 to 25 wt. %, e.g., from 0.5 to 15 wt. %, or from 1.0 to 10 wt. %. For purposes of the present specification, unless otherwise indicated, weight percent is based on the total weight the catalyst including metal and support.

In some embodiments, the catalyst contains at least two active metals in addition to the precious metal. The at least two active metals may be selected from any of the active metals identified above, so long as they are not the same as the precious metal or each other. Additional active metals may also be used in some embodiments. Thus, in some embodiments, there may be multiple active metals on the support in addition to the precious metal.

Preferred bimetallic (precious metal+active metal) combinations for some exemplary catalyst compositions include platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, rhodium/iron, rhodium/cobalt, rhodium/nickel and rhodium/tin. In some embodiments, the catalyst comprises three metals on a support, e.g., one precious metal and two active metals. Exemplary tertiary combinations may include palladium/rhenium/tin, palladium/rhenium/cobalt, palladium/rhenium/nickel, palladium/cobalt/tin, platinum/tin/palladium, platinum/tin/rhodium, platinum/tin/gold, platinum/tin/iridium, platinum/cobalt/tin, platinum/tin/copper, platinum/tin/chromium, platinum/tin/zinc, platinum/tin/nickel, rhodium/nickel/tin, rhodium/cobalt/tin and rhodium/iron/tin. In one preferred embodiment, the tertiary combination comprises cobalt or tin or both cobalt and tin. In some embodiments, the catalyst may comprise more than three metals on the support.

When the catalyst comprises a precious metal and one active metal on a support, the active metal optionally is present in an amount from 0.1 to 20 wt. %, e.g., from 0.1 to 10 wt. %, or from 0.1 to 5 wt. %. When the catalyst comprises two or more active metals in addition to the precious metal, e.g., a first active metal and a second active metal, the first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 5 wt. %. If the catalyst further comprises a third active metal, the third active metal may be present in an amount from 0.05 to 20 wt. %, e.g., from 0.05 to 10 wt. %, or from 0.05 to 3 wt. %. The active metals may be alloyed with one another or may comprise a non-alloyed metal solution, a metal mixture or be present as one or more metal oxides.

The preferred metal ratios may vary somewhat depending on the active metals used in the catalyst. In some embodiments, the mole ratio of the precious metal to the one or more active metals is from 10:1 to 1:10, e.g., from 4:1 to 1:4, from 2:1 to 1:2 or from 1.5:1 to 1:1.5. In another embodiment, the precious metal may be present in an amount from 0.1 to 5 wt. %, the first active metal in an amount from 0.5 to 20 wt. % and the second active metal in an amount from 0.5 to 20 wt. %, based on the total weight of the catalyst. In another embodiment, the precious metal is present in an amount from 0.1 to 5 wt. %, the first active metal in an amount from 0.5 to 1.5 wt. % and the second active metal in an amount from 0.5 to 1.5 wt. %, In one embodiment, the first and second active metals are present as cobalt and tin, and are present at a cobalt to tin molar ratio from 6:1 to 1:6 or from 3:1 to 1:3. In another embodiment, the cobalt and tin are present in substantially equimolar amounts.

The catalysts of the present invention comprise a suitable support material, preferably a modified support material. In one embodiment, the support material may be an inorganic oxide. In one embodiment, the support material may be selected from the group consisting of silica, alumina, titania, silica/alumina, pyrogenic silica, high purity silica, zirconia, carbon (e.g., carbon black or activated carbon) zeolites and mixtures thereof. Preferably, the support material comprises silica. In preferred embodiments, the support material is present in an amount from 25 wt. % to 99 wt. %, e.g., from 30 wt. % to 98 wt. % or from 35 wt. % to 95 wt. %, based on the total weight of the catalyst.

In preferred embodiments, the support material comprises a siliceous support material, e.g., silica, having a surface area of at least 50 $m^2/g$, e.g., at least 100 $m^2/g$, at least 150 $m^2/g$, at least 200 $m^2/g$ or at least 250 $m^2/g$. In terms of ranges, the siliceous support material preferably has a surface area from 50 to 600 $m^2/g$, e.g., from 100 to 500 $m^2/g$ or from 100 to 300 $m^2/g$. High surface area silica, as used throughout the application, refers to silica having a surface area of at least 250 $m^2/g$. For purposes of the present specification, surface area refers to BET nitrogen surface area, meaning the surface area as determined by ASTM D6556-04, the entirety of which is incorporated herein by reference.

The preferred siliceous support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 cm$^3$/g, e.g., from 0.7 to 1.5 cm$^3$/g or from 0.8 to 1.3 cm$^3$/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the siliceous support material has a morphology that allows for a packing density from 0.1 to 1.0 g/cm$^3$, e.g., from 0.2 to 0.9 g/cm$^3$ or from 0.3 to 0.8 g/cm$^3$. In terms of size, the silica support material preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the precious metal and the one or more active metals that are disposed on the support are generally in the form of very small metal (or metal oxide) particles or crystallites relative to the size of the support, these metals should not substantially impact the size of the overall catalyst particles. Thus, the above particle sizes generally apply to both the size of the support as well as to the final catalyst particles, although the catalyst particles are preferably processed to form much larger catalyst particles, e.g., extruded to form catalyst pellets.

A preferred silica support material is SS61138 High Surface Area (HSA) Silica Catalyst Carrier from Saint-Gobain N or Pro. The Saint-Gobain N or Pro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$.

A preferred silica/alumina support material is KA-160 (Süd Chemie) silica spheres having a nominal diameter of about 5 mm, a density of about 0.562 g/ml, in absorptivity of about 0.583 g H$_2$O/g support, a surface area of about 160 to 175 m$^2$/g, and a pore volume of about 0.68 ml/g.

The support material preferably comprises a support modifier. A support modifier may adjust the acidity of the support material. In another embodiment, the support modifier may be a basic modifier that has a low volatility or no volatility. In one embodiment, the support modifiers are present in an amount from 0.1 wt. % to 50 wt. %, e.g., from 0.2 wt. % to 25 wt. %, from 0.5 wt. % to 15 wt. %, or from 1 wt. % to 12 wt. %, based on the total weight of the catalyst.

As indicated, the support modifiers may adjust the acidity of the support. For example, the acid sites, e.g., Brønsted acid sites or Lewis acid sites, on the support material may be adjusted by the support modifier to favor selectivity to ethanol during the hydrogenation of acetic acid and/or esters thereof. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In general, the surface acidity of the support may be adjusted based on the composition of the feed stream being sent to the hydrogenation process in order to maximize alcohol production, e.g., ethanol production.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof.

Acidic support modifiers include those selected from the group consisting of TiO$_2$, ZrO$_2$, Nb$_2$O$_5$, Ta$_2$O$_5$, Al$_2$O$_3$, B$_2$O$_3$, P$_2$O$_5$, and Sb$_2$O$_3$. Preferred acidic support modifiers include those selected from the group consisting of TiO$_2$, ZrO$_2$, Nb$_2$O$_5$, Ta$_2$O$_5$, and Al$_2$O$_3$. The acidic modifier may also include those selected from the group consisting of WO$_3$, MoO$_3$, V$_2$O$_5$, VO$_2$, V$_2$O$_3$, Nb$_2$O$_5$, Ta$_2$O$_5$, FeO, Fe$_3$O$_4$, Fe$_2$O$_3$, Cr$_2$O$_3$, MnO$_2$, CoO, Co$_2$O$_3$, and Bi$_2$O$_3$. Reduced tungsten oxides or molybdenum oxides may also be employed, such as, for example, one or more of W$_{20}$O$_{58}$, WO$_2$, W$_{49}$O$_{119}$, W$_{50}$O$_{148}$, W$_{18}$O$_{49}$, MO$_9$O$_{26}$, MO$_8$O$_{23}$, MO$_5$O$_{14}$, MO$_{17}$O$_{47}$, MO$_4$O$_{11}$, or MoO$_2$. It has now surprisingly and unexpectedly been discovered that the use of such metal oxide support modifiers in combination with a precious metal and one or more active metals may result in catalysts having multifunctionality, and which may be suitable for converting a carboxylic acid, such as acetic acid, as well as corresponding esters thereof, e.g., ethyl acetate, to one or more hydrogenation products, such as ethanol, under hydrogenation conditions.

In some embodiments, the acidic support modifier comprises a mixed metal oxide comprising at least one of the active metals and an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, copper tungstate, iron tungstate, zirconium tungstate, manganese tungstate, cobalt molybdate, copper molybdate, iron molybdate, zirconium molybdate, manganese molybdate, cobalt vanadate, copper vanadate, iron vanadate, zirconium vanadate, manganese vanadate, cobalt niobate, copper niobate, iron niobate, zirconium niobate, manganese niobate, cobalt tantalate, copper tantalate, iron tantalate, zirconium tantalate, and manganese tantalate. It has now been discovered that catalysts containing such mixed metal support modifiers may provide the desired degree of multifunctionality at increased conversion, e.g., increased ester conversion, and with reduced byproduct formation, e.g., reduced diethyl ether formation.

In one embodiment, the catalyst comprises from 0.25 to 1.25 wt. % platinum, from 1 to 10 wt. % cobalt, and from 1 to 10 wt. % tin on a silica or a silica-alumina support material. The support material may comprise from 5 to 15 wt. % acidic support modifiers, such as WO$_3$, V$_2$O$_5$ and/or MoO$_3$. In one embodiment, the acidic modifier may comprise cobalt tungstate, e.g., in an amount from 5 to 15 wt. %.

In some embodiments, the modified support comprises one or more active metals in addition to one or more acidic modifiers. The modified support may, for example, comprise one or more active metals selected from copper, iron, cobalt, vanadium, nickel, titanium, zinc, chromium, molybdenum, tungsten, tin, lanthanum, cerium, and manganese. For example, the support may comprise an active metal, preferably not a precious metal, and an acidic or basic support modifier. Preferably, the support modifier comprises a support modifier metal selected from the group consisting of tungsten, molybdenum, vanadium, niobium, and tantalum. In this aspect, the final catalyst composition comprises a precious metal, and one or more active metals disposed on the modified support. In a preferred embodiment, at least one of the active metals in the modified support is the same as at least one of the active metals disposed on the support. For example, the catalyst may comprise a support modified with cobalt, tin and tungsten (optionally as $WO_3$ and/or as cobalt tungstate). In this example, the catalyst further comprises a precious metal, e.g., palladium, platinum or rhodium, and at least one active metal, e.g., cobalt and/or tin, disposed on the modified support.

Using an increase hydrogen flow and a mixed feed of acetic acid and ethyl acetate, the hydrogenation in the first reactor may achieve favorable conversion of acetic acid and ethyl acetate. For purposes of the present invention, the term "conversion" refers to the amount of acetic acid or ethyl acetate in the feed that is converted to a compound other than acetic acid or ethyl acetate, respectively. Conversion is expressed as a percentage based on acetic acid and/or ethyl acetate in the feed. The conversion of acetic acid may be at least 10%, e.g., at least 20%, at least 40%, at least 50%, at least 60%, at least 70% or at least 80%. The conversion of ethyl acetate acid preferably is greater than 0%, meaning that more ethyl acetate is consumed than produced. In other embodiments the ethyl acetate conversion is greater than or equal to 0%. During the hydrogenation of acetic acid, ethyl acetate may be produced. Without consuming any ethyl acetate from the mixed vapor phase reactants, the conversion of ethyl acetate would be negative, meaning that more ethyl acetate would be produced. However, for purposes of the present invention, enough of the ethyl acetate is consumed to at least offset the produced ethyl acetate. Thus, preferably conversion of ethyl acetate may be greater than or equal to 0%, e.g., at least 5%, at least 10%, at least 20%, or at least 35%. Although catalysts that have high conversions are desirable, especially acetic acid conversions that are at least 80% or at least 90%, in some embodiments a low acetic acid conversion may be acceptable at high selectivity for ethanol. It is, of course, well understood that in many cases, it is possible to compensate for low acetic acid conversion by appropriate recycle streams or use of larger reactors, but it is more difficult to compensate for poor selectivity.

Selectivity is expressed as a mole percent based on converted reactant, e.g., acetic acid or ethyl acetate. It should be understood that each compound converted from acetic acid or ethyl acetate has an independent selectivity and that selectivity is independent from conversion. For example, if 60 mole % of the converted acetic acid is converted to ethanol, we refer to the ethanol selectivity as 60%. Total selectivity is based on the combined converted acetic acid and ethyl acetate. Preferably, the catalyst total selectivity to ethanol is at least 60%, e.g., at least 70%, or at least 80%. More preferably, in the reactor, the total selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the reactor, before any subsequent processing, such as purification and separation, will typically comprise unreacted acetic acid, ethyl acetate, ethanol, and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 30 | 5 to 28 | 10 to 26 | 10 to 22 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

Separation

Returning to FIG. 1, the hydrogenation reactor produces a crude ethanol product that is withdrawn, preferably continuously, from reactor 108 via line 120 and directed to separation zone 104. Separation zone 104 comprises flasher 122. The crude ethanol product may be condensed and fed to flasher 122, which, in turn, provides a vapor stream and a liquid stream. Flasher 122 may operate at a temperature of from 20° C. to 250° C., e.g., from 30° C. to 250° C. or from 60° C. to 200° C. The pressure of flasher 122 may be from 50 kPa to 2000 kPa, e.g., from 75 kPa to 1500 kPa or from 100 kPa to 1000 kPa.

The vapor stream exiting flasher 122 may comprise hydrogen and hydrocarbons, at least a portion of which may be purged and/or returned to reaction zone 102 via line 124. The returned portion of the vapor stream may pass through a compressor. The returned portion of the vapor stream and may be combined with the hydrogen feed line 110 and co-fed to vaporizer 106.

The liquid from flasher 122 is withdrawn and pumped as a feed composition via line 126 to the hydrogenation separation zone 104. Exemplary compositions of line 126 are provided in Table 2. It should be understood that liquid line 126 may contain other components, not listed, such as additional components in the feed.

TABLE 2

FEED COMPOSITION

|  | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 0 to 50 | 0 to 35 |
| Water | 5 to 30 | 5 to 28 | 10 to 26 |
| Ethyl Acetate | <30 | 0.001 to 25 | 1 to 12 |
| Acetaldehyde | <10 | 0.001 to 3 | 0.1 to 3 |
| Acetal | 0.01 to 10 | 0.001 to 6 | 0.01 to 5 |
| Acetone | <5 | 0.0005 to 0.05 | 0.001 to 0.03 |
| Other Alcohols | <5 | <0.005 | <0.001 |
| Other Esters | <5 | <0.005 | <0.001 |
| Other Ethers | <5 | <0.005 | <0.001 |

The amounts indicated as less than (<) in the tables throughout the present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 3 may include, but are not limited to, methanol, isopropanol, n-propanol, n-butanol, 2-butanol or mixtures thereof. In one embodiment, the feed composition, e.g., line 126, may comprise propanol, e.g., isopropanol and/or n-propanol, in an amount from 0.001 to 0.1 wt. %, from 0.001 to 0.05 wt. % or from 0.001 to 0.03 wt. %. It should be understood that these other components may be carried through in any of the distillate or residue streams described herein.

Optionally, the crude ethanol product may pass through one or more membranes to separate hydrogen and/or other non-condensable gases. In other optional embodiments, the crude ethanol product may be fed directly to the acid separation column as a vapor feed and the non-condensable gases may be recovered from the overhead of the column.

Figure 2:
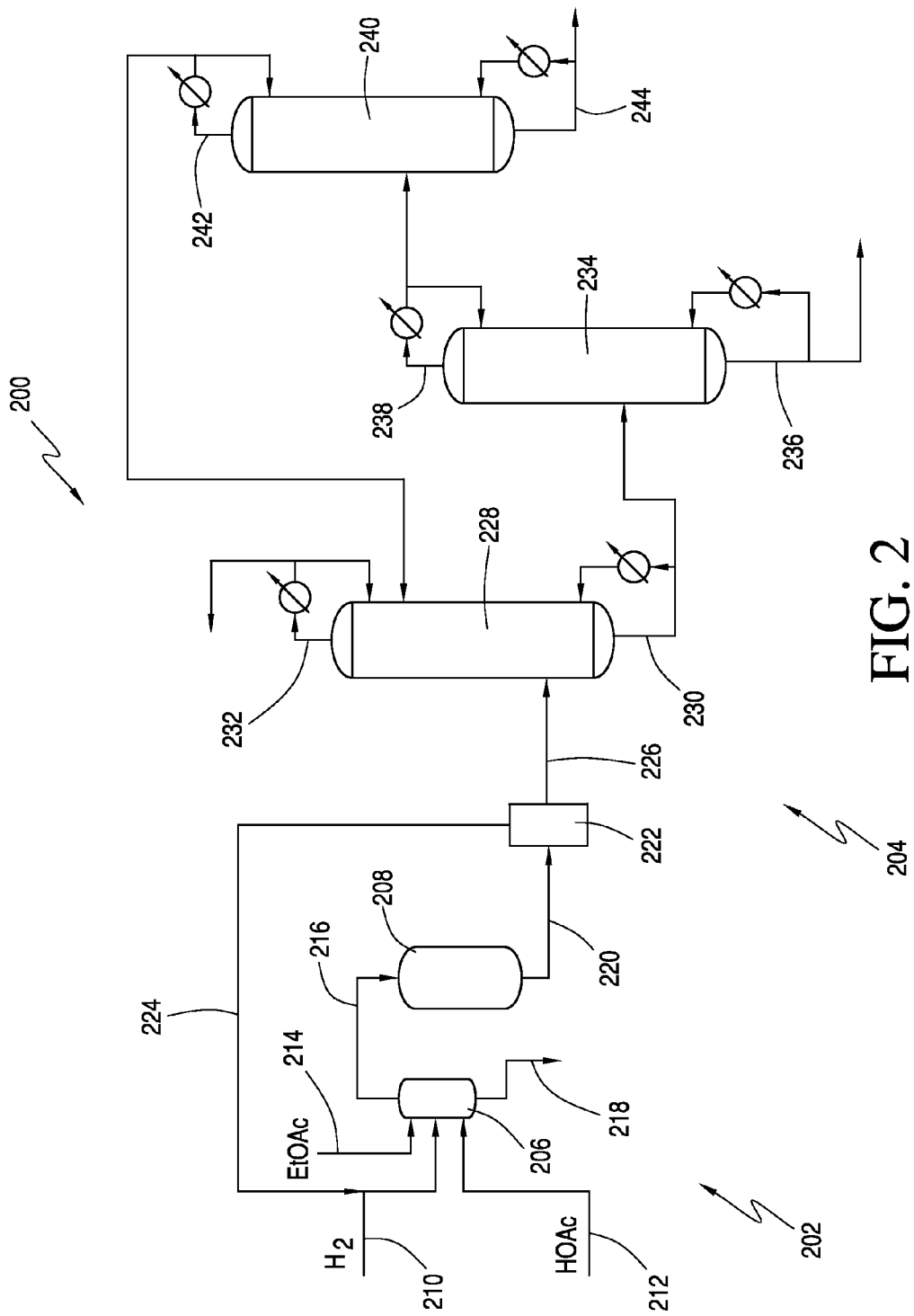
FIG. 2 is a schematic diagram of a hydrogenation/separation process in accordance with an embodiment of the present invention.

Ethanol produced by the reactor may be recovered using various different techniques. In FIG. 1, the separation of the crude ethanol product uses two columns with an intervening water separation. In FIG. 2, the separation of the crude ethanol product uses three columns. Other separation systems may also be used with embodiments of the present invention. In FIG. 2, the components of the reaction zone and the flasher are similar and perform similar functions to the corresponding components in FIG. 1.

FIG. 1 illustrates an exemplary separation system. In FIG. 2, crude ethanol stream 126 is withdrawn from flasher 122 and pumped to the side of first column 128. In one preferred embodiment, the hydrogenation reaction zone operates at above 80% acetic acid conversion, e.g., above 90% conversion or above 99% conversion. Thus, the acetic acid concentration in the liquid stream 126 may be low.

Liquid stream 126 is introduced in the middle or lower portion of first column 128, also referred to as an acid-water column. For purposes of convenience, the columns in each exemplary separation process, may be referred as the first, second, third, etc., columns, but it is understood that first column 128 in FIG. 1 operates differently than the first column 228 of FIG. 2. In one embodiment, no entrainers are added to first column 128. In FIG. 2, first column 128, water and unreacted acetic acid, along with any other heavy components, if present, are removed from liquid stream 126 and are withdrawn, preferably continuously, as a first residue in line 130. Preferably, a substantial portion of the water in the crude ethanol product that is fed to first column 128 may be removed in the first residue, for example, up to about 75% or to about 90% of the water from the crude ethanol product. Optionally, some of line 130, e.g., a small amount, may be also recycled to vaporizer the hydrogenation reaction zone. Optionally, at least a portion of residue in line 130 may be purged from the system. Reducing the amount of heavies to be purged may improve efficiencies of the process while reducing byproducts. First column 128 also forms a first distillate, which is withdrawn in line 132.

When column 128 is operated under about 170 kPa, the temperature of the residue exiting in line 130 preferably is from 90° C. to 130° C., e.g., from 95° C. to 120° C. or from 100° C. to 115° C. The temperature of the distillate exiting in line 132 preferably is from 60° C. to 90° C., e.g., from 65° C. to 85° C. or from 70° C. to 80° C. In some embodiments, the pressure of first column 128 may range from 0.1 kPa to 510 kPa, e.g., from 1 kPa to 475 kPa or from 1 kPa to 375 kPa.

The first distillate in line 132 comprises water, in addition to ethanol and other organics. In terms of ranges, the concentration of water in the first distillate in line 132 preferably is from 4 wt. % to 38 wt. %, e.g., from 7 wt. % to 32 wt. %, or from 7 to 25 wt. %. A portion of first distillate in line 132 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 128. The condensed portion of the first distillate in line 134 may optionally also be combined with line 136, discussed below, and fed to second column 138.

The remaining portion of the first distillate in line 132 is fed to water separation unit 140. Water separation unit 140 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 140 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. Water separator 140 may remove at least 95% of the water from the portion of first distillate in line 132, and more preferably from 99% to 99.99% of the water from the first distillate, in a water stream 142. All or a portion of water stream 142 may be returned to column 128 in line 144, where the water preferably is ultimately recovered from column 128 in the first residue in line 130. Additionally or alternatively, all or a portion of water stream 142 may be purged. The remaining portion of first distillate 132 exits the water separator 140 as ethanol mixture stream 146. Ethanol mixture stream 146 may have a low concentration of water of less than 10 wt. %, e.g., less than 6 wt. % or less than 2 wt. %. Exemplary components of ethanol mixture stream 146 and first residue in line 130 are provided in Table 2 below. It should also be understood that these streams may also contain other components, not listed, such as components derived from the feed.

TABLE 2

FIRST COLUMN 128 WITH PSA (FIG. 1)

|  | Conc. (wt. %) | Conc. (wt. %) | Conc. (wt. %) |
|---|---|---|---|
| Ethanol Mixture Stream | | | |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | <90 | 1 to 50 | 2 to 35 |
| Water | 30 to 99 | 45 to 95 | 60 to 90 |
| Ethanol | <1 | <0.9 | <0.3 |

Preferably, ethanol mixture stream 136 is not returned or refluxed to first column 128. The condensed portion of the first distillate in line 134 may be combined with ethanol mixture stream 136 to control the water concentration fed to the second column 138. For example, in some embodiments the first distillate may be split into equal portions, while in other embodiments, all of the first distillate may be condensed or all of the first distillate may be processed in the water separation unit. In FIG. 1, the condensed portion in line 134 and ethanol mixture stream 136 are co-fed to second column 138. In other embodiments, the condensed portion in line 134 and ethanol mixture stream 136 may be separately fed to second column 138. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 138 in FIG. 1, also referred to as the "light ends column," removes ethyl acetate and acetaldehyde from the first distillate in line 132 and/or ethanol mixture stream 136. Ethyl acetate and acetaldehyde are removed as a second distillate in line 146 and ethanol is removed as the second residue in line 148. Optionally, the second distillate in line 146 may be recycled to reaction zone 102 and fed to reactor 208 (not shown). Second column 138 may be a tray column or packed column. In one embodiment, second column 138 is a tray column having from 5 to 70 trays, e.g., from 15 to 50 trays or from 20 to 45 trays.

Second column 138 operates at a pressure ranging from 0.1 kPa to 510 kPa, e.g., from 10 kPa to 450 kPa or from 50 kPa to 350 kPa. Although the temperature of second column 138 may vary, when at about 20 kPa to 70 kPa, the temperature of the second residue exiting in line 148 preferably is from 30° C. to 75° C., e.g., from 35° C. to 70° C. or from 40° C. to 65° C. The temperature of the second distillate exiting in line 146 preferably is from 20° C. to 55° C., e.g., from 25° C. to 50° C. or from 30° C. to 45° C.

The total concentration of water fed to second column 138 preferably is less than 10 wt. %, as discussed above. When first distillate in line 132 and/or ethanol mixture stream comprises minor amounts of water, e.g., less than 1 wt. % or less than 0.5 wt. %, additional water may be fed to the second column 138 as an extractive agent in the upper portion of the column, e.g., via extractive agent feed 150. A sufficient amount of water is preferably added via the extractive agent such that the total concentration of water fed to second column 138 is from 1 to 10 wt. % water, e.g., from 2 to 6 wt. %, based on the total weight of all components fed to second column 138. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate and second residue compositions for the second column 138 are provided in Table 3, below. It should be understood that the distillate and residue may also contain other components, not listed in Table 3.

TABLE 3

SECOND COLUMN 138 (FIG. 1)

|  | Conc. (wt. %) | Conc. (wt. %) | Conc. (wt. %) |
|---|---|---|---|
| Second Distillate | | | |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue | | | |
| Ethanol | 80 to 99.5 | 85 to 97 | 60 to 95 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |

The second residue in FIG. 1 comprises one or more impurities selected from the group consisting of ethyl acetate, acetic acid, acetaldehyde, and diethyl acetal. The second residue may comprise at least 100 wppm of these impurities, e.g., at least 250 wppm or at least 500 wppm. In some embodiments, the second residue may contain substantially no ethyl acetate or acetaldehyde.

The second distillate in line 146, which comprises ethyl acetate and/or acetaldehyde, preferably is refluxed as shown in FIG. 1, for example, at a reflux ratio of from 1:30 to 30:1, e.g., from 1:10 to 10:1 or from 1:3 to 3:1. In one aspect, not shown, the second distillate 146 or a portion thereof may be returned to the hydrogenation reactor. The ethyl acetate and/or acetaldehyde in the second distillate may be further reacted in the hydrogenation reactor.

In one embodiment, the second distillate in line 146 and/or a refined second distillate, or a portion of either or both streams, may be further separated to produce an acetaldehyde-containing stream and an ethyl acetate-containing stream. This may allow a portion of either the resulting acetaldehyde-containing stream or ethyl acetate-containing stream to be recycled to the hydrogenation reactor while purging the other stream. The purge stream may be valuable as a source of either ethyl acetate and/or acetaldehyde.

FIG. 2 illustrates another exemplary separation system. In FIG. 2, crude ethanol stream 226 is withdrawn from a flasher 222 and pumped to the side of first column 228. In one preferred embodiment, the hydrogenation reaction zone operates at above 80% acetic acid conversion, e.g., above 90% conversion or above 99% conversion. Thus, the acetic acid concentration in the liquid stream 226 may be low.

In the exemplary embodiment shown in FIG. 2, liquid stream 226 is introduced in the lower part of first column 228, e.g., lower half or middle third. In one embodiment, no entrainers are added to first column 228. In first column 228, a weight majority of the ethanol, water, acetic acid, and other heavy components, if present, are removed from liquid stream 226 and are withdrawn, preferably continuously, as residue in line 230.

First column 228 also forms an overhead distillate, which is withdrawn in line 232, and which may be condensed and refluxed, for example, at a ratio of from 30:1 to 1:30, e.g., from 10:1 to 1:10 or from 1:5 to 5:1. The overhead distillate in stream 232 preferably comprises a weight majority of the ethyl acetate from liquid stream 226. Overhead distillate in stream 232 may be combined with a recycle line from column 234 as discussed below, and returned to the reaction zone.

When column 228 is operated under about 170 kPa, the temperature of the residue exiting in line 230 preferably is from 70° C. to 155° C., e.g., from 90° C. to 130° C. or from 100° C. to 110° C. The base of column 228 may be maintained at a relatively low temperature by withdrawing a residue stream comprising ethanol, water, and acetic acid, thereby providing an energy efficiency advantage. The temperature of the distillate exiting in line 232 from column 228 preferably at 170 kPa is from 75° C. to 100° C., e.g., from 75° C. to 83° C. or from 81° C. to 84° C. In some embodiments, the pressure of first column 228 may range from 0.1 kPa to 510 kPa, e.g., from 1 kPa to 475 kPa or from 1 kPa to 375 kPa. Exemplary components of the distillate and residue compositions for first column 228 are provided in Table 4 below. It should also be understood that the distillate and residue may also contain other components, not listed in Table 4.

TABLE 4

FIRST COLUMN 228 (FIG. 2)

|  | Conc. (wt. %) | Conc. (wt. %) | Conc. (wt. %) |
|---|---|---|---|
| Distillate |  |  |  |
| Ethyl Acetate | 10 to 85 | 15 to 80 | 20 to 75 |
| Acetaldehyde | 0.1 to 70 | 0.2 to 65 | 0.5 to 65 |
| Acetal | <0.1 | <0.1 | <0.05 |
| Acetone | <0.05 | 0.001 to 0.03 | 0.01 to 0.025 |
| Ethanol | 3 to 55 | 4 to 50 | 5 to 45 |
| Water | 0.1 to 20 | 1 to 15 | 2 to 10 |
| Acetic Acid | <2 | <0.1 | <0.05 |
| Residue |  |  |  |
| Acetic Acid | 0.01 to 35 | 0.1 to 30 | 0.2 to 25 |
| Water | 5 to 40 | 10 to 35 | 15 to 30 |
| Ethanol | 10 to 75 | 15 to 70 | 20 o 65 |

In an embodiment of the present invention, column 228 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 230 to water in the distillate in line 232 may be greater than 1:1, e.g., greater than 2:1. The weight ratio of ethanol in the residue to ethanol in the distillate may be greater than 1:1, e.g., greater than 2:1

The amount of acetic acid in the first residue may vary depending primarily on the conversion in the hydrogenation reactor. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 wppm, less than 500 wppm or less than 100 wppm acetic acid. The distillate may be purged from the system or recycled in whole or part to the hydrogenation reactor. In some embodiments, the distillate may be further separated, e.g., in a distillation column (not shown), into an acetaldehyde stream and an ethyl acetate stream. Either of these streams may be returned to the hydrogenation reactor or separated as a separate product.

Some species, such as acetals, may decompose in first column 228 such that very low amounts, or even no detectable amounts, of acetals remain in the distillate or residue.

To recover ethanol, the residue in line 230 may be further separated in second column 234, also referred to as an "acid separation column." An acid separation column may be used when the acetic acid concentration in the first residue is greater than 1 wt. %, e.g., greater than 5 wt. %. The first residue in line 230 is introduced to second column 234 preferably in the top part of column 234, e.g., top half or top third. Second column 234 yields a second residue in line 236 comprising acetic acid and water, and a second distillate in line 238 comprising ethanol.

Second column 234 may be a tray column or packed column. In one embodiment, second column 234 is a tray column having from 5 to 150 trays, e.g., from 15 to 50 trays or from 20 to 45 trays. Although the temperature and pressure of second column 234 may vary, when at atmospheric pressure the temperature of the second residue exiting in line 236 preferably is from 95° C. to 130° C., e.g., from 100° C. to 125° C. or from 110° C. to 120° C. The temperature of the second distillate exiting in line 238 preferably is from 60° C. to 105° C., e.g., from 75° C. to 100° C. or from 80° C. to 100° C. The pressure of second column 234 may range from 0.1 kPa to 510 kPa, e.g., from 1 kPa to 475 kPa or from 1 kPa to 375 kPa. Exemplary components for the distillate and residue compositions for second column 234 are provided in Table 5 below. It should be understood that the distillate and residue may also contain other components, not listed in Table 5.

TABLE 5

SECOND COLUMN 234 (FIG. 2)

|  | Conc. (wt. %) | Conc. (wt. %) | Conc. (wt. %) |
|---|---|---|---|
| Second Distillate |  |  |  |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 1 to 25 | 5 to 20 |
| Second Residue |  |  |  |
| Acetic Acid | 0.1 to 45 | 0.2 to 40 | 0.5 to 35 |
| Water | 45 to 99.9 | 55 to 99.8 | 65 to 99.5 |
| Ethyl Acetate | <2 | <1 | <0.5 |
| Ethanol | <5 | 0.001 to 5 | <2 |

The weight ratio of ethanol in the second distillate in line 238 to ethanol in the second residue in line 236 preferably is at least 35:1. In one embodiment, the weight ratio of water in the second residue 236 to water in the second distillate 238 is greater than 2:1, e.g., greater than 4:1 or greater than 6:1. In addition, the weight ratio of acetic acid in the second residue 236 to acetic acid in the second distillate 238 preferably is greater than 10:1, e.g., greater than 15:1 or greater than 20:1. Preferably, the second distillate in line 238 is substantially free of acetic acid and may only contain, if any, trace amounts of acetic acid.

As shown, the second distillate in line 238 is fed to optional third column 240, e.g., ethanol product column, for separating the second distillate into a third distillate (ethyl acetate distillate) in line 242 and a third residue (ethanol residue) in line 344. Although FIG. 2 shows 240, column 240 is not required to implement the present invention. In one embodiment (not shown) the separation zone comprises a first column, e.g., column 228, and second column, e.g., column 234, and does not include a third column. Second distillate in line 238 may be introduced into the lower part of column 240, e.g., lower half or lower third. Third distillate 242 is preferably refluxed, for example, at a reflux ratio greater than 2:1, e.g., greater than 5:1 or greater than 10:1. Additionally, at least a portion of third distillate 242 may be purged. Third column 240 is preferably a tray column as described herein and preferably operates at atmospheric pressure. The temperature of the third residue exiting from third column 240 preferably is from 60° C. to 110° C., e.g., from 70° C. to 100° C. or from 75° C. to 95° C. The temperature of the third distillate exiting from third column 240 preferably is from 70° C. to 115° C., e.g., from 80° C. to 110° C. or from 85° C. to 105° C., when the column is operated at atmospheric pressure.

The remaining water from the second distillate in line 238 may be removed in further embodiments of the present invention. Depending on the water concentration, the ethanol product may be derived from the second distillate in line 238. Some applications, such as industrial ethanol applications, may tolerate water in the ethanol product, while other applications, such as fuel applications, may require an anhydrous ethanol. The amount of water in the distillate of line 238 may be closer to the azeotropic amount of water, e.g., at least 4 wt. %, preferably less than 20 wt. %, e.g., less than 12 wt. % or less than 7.5 wt. %. Water may be removed from the second distillate in line 238 using several different separation techniques as described herein. Particularly preferred techniques include the use of distillation column, membranes, adsorption units, and combinations thereof.

The columns shown in FIGS. 1 and 2 may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 2000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

The ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 6.

TABLE 6

FINISHED ETHANOL COMPOSITIONS

| Component | Conc. (wt. %) | Conc. (wt. %) | Conc. (wt. %) |
| --- | --- | --- | --- |
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 11, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0020002 and 2010/0020001, the entireties of which is incorporated herein by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,144 and zeolite Y in U.S. Pat. No. 3,130,007, the entireties of which are hereby incorporated herein by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising:
   (a) reacting acetic acid, ethyl acetate, and hydrogen in one reactor and in the presence of one catalyst under conditions effective to form a crude ethanol product comprising ethanol, acetic acid, ethyl acetate, and water; and
   (b) recovering ethanol from the crude ethanol product;
   wherein the molar ratio of hydrogen to acetic acid fed to the reactor is greater than 12:1;
   and wherein ethyl acetate conversion is greater than or equal to 0%.

2. The process of claim 1, further comprising the step of:
   maintaining the reactants in the reactor for a residence time less than 20 seconds.

3. The process of claim 2, wherein the residence time is less than 17 seconds.

4. The process of claim 1, wherein acetic acid conversion is greater than 60%.

5. The process of claim 1, wherein acetic acid conversion is greater than 70%.

6. The process of claim 1, wherein the acetic acid, the ethyl acetate, and the hydrogen comprise a reaction mixture and wherein the reaction mixture comprises greater than 20 wt. % hydrogen.

7. The process of claim 1, wherein the acetic acid is formed from methanol and carbon monoxide, wherein each of the methanol, the carbon monoxide, and the hydrogen for the hydrogenating step is derived from syngas, and wherein the syngas is derived from a carbon source selected from the group consisting of natural gas, oil, petroleum, coal, biomass, and combinations thereof.

8. The process of claim 1, wherein the catalyst comprises one or more precious metals on a support.

9. The process of claim 8, wherein the one or more precious metals is selected from the group consisting of rhodium, platinum, palladium, osmium, iridium, gold, rhenium, and ruthenium.

10. The process of claim 8, wherein the catalyst further comprises one or more active metals different from the one or more precious metals.

11. The process of claim 10, wherein the one or more active metals is selected from the group consisting of copper, iron, cobalt, vanadium, nickel, titanium, zinc, chromium, molybdenum, tungsten, tin, lanthanum, cerium, manganese, rhodium, platinum, palladium, osmium, iridium, gold, and ruthenium.

12. The process of claim 10, wherein the precious metals/active metal combination is selected from the group consisting of platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, palladium/rhenium/tin, palladium/rhenium/cobalt, palladium/rhenium/nickel, palladium/cobalt/tin, platinum/tin/palladium, platinum/tin/rhodium, platinum/tin/gold, platinum/tin/iridium, platinum/cobalt/tin, platinum/tin/copper, platinum/tin/chromium, platinum/tin/zinc, and platinum/tin/nickel.

13. A process of claim 8, wherein the support is selected from the group consisting of silica, alumina, silica/alumina, calcium metasilicate, zirconia, carbon, zeolites and mixtures thereof.

14. The process of claim 8, wherein the catalyst further comprises a support modifier.

15. A process of claim 1, wherein the reactants are fed to the reactor at a gas hourly space velocity (GHSV) from 180 $hr^{-1}$ to 50,000 $hr^{-1}$.

16. The process of claim 13, wherein the silica comprises pyrogenic silica, high purity silica.

* * * * *